(12) United States Patent
Vieweg (10) Patent No.: US 11,090,742 B2
(45) Date of Patent: Aug. 17, 2021

(54) METHOD FOR MACHINING A RACK AND RACK MACHINED ACCORDING TO SAID METHOD

(71) Applicant: MVO GMBH METALLVERARBEITUNG OSTALB, Schwaebisch Gmuend (DE)

(72) Inventor: Niels Vieweg, Neusaess (DE)

(73) Assignee: MVO GMBH METALLVERARBEITUNG OSTALB, Schwaebisch Gmuend (DE)

( * ) Notice: Subject to any disclaimer, the term of this patent is extended or adjusted under 35 U.S.C. 154(b) by 0 days.

(21) Appl. No.: 16/068,712

(22) PCT Filed: Sep. 23, 2017

(86) PCT No.: PCT/DE2017/000316
§ 371 (c)(1),
(2) Date: Jul. 9, 2018

(87) PCT Pub. No.: WO2018/077318
PCT Pub. Date: May 3, 2018

(65) Prior Publication Data
US 2020/0114440 A1    Apr. 16, 2020

(30) Foreign Application Priority Data
Oct. 28, 2016    (DE) .................. 10 2016 012 941.7

(51) Int. Cl.
*C21D 7/06* (2006.01)
*B23F 5/08* (2006.01)
(Continued)

(52) U.S. Cl.
CPC .................. *B23F 5/08* (2013.01); *B62D 3/12* (2013.01); *C07D 307/68* (2013.01); *C21D 7/06* (2013.01); *C21D 9/32* (2013.01)

(58) Field of Classification Search
CPC ........... B23F 5/08; B62D 3/12; C07D 307/68; C21D 7/06; C21D 9/32
(Continued)

(56) References Cited

U.S. PATENT DOCUMENTS 3,313,172 A * 4/1967 Ulrich, Jr. et al.
5,297,418 A * 3/1994 Champaigne
(Continued)

FOREIGN PATENT DOCUMENTS

AT         515352 T      8/2015
DE      19500078 A1      7/1996
(Continued)

OTHER PUBLICATIONS

NPL-1: Errichello, Measuring Residual Stress in Gears, Gear Technology, Mar./Apr. 2015, pp. 50-51 (Year: 2015).*
(Continued)

*Primary Examiner* — Jie Yang
(74) *Attorney, Agent, or Firm* — Cohen & Hildebrand, PLLC (57) ABSTRACT

The invention relates to a method for machining a rack and to a rack (1) machined according to said method, for example a steering rack. In said method, the stress pattern that is present after hardening and/or straightening the rack and that has a chaotic internal stress distribution of tensile and compressive stresses is converted into a stress pattern that optimizes the strength and the use of the material and also the diameter of the rack, such that, without altering the structure, at least the region of the gear teeth (2) is pre-stressed, in a functionally combined series of steps of a machining pass, with a deliberately introduced internal compressive stress without tensile stress and with a predominantly uniform stress distribution or stress plane.

19 Claims, 7 Drawing Sheets

(51) Int. Cl.
*B62D 3/12* (2006.01)
*C21D 9/32* (2006.01)
*C07D 307/68* (2006.01)

(58) Field of Classification Search
USPC ........................................................ 148/573
See application file for complete search history.

(56) References Cited

U.S. PATENT DOCUMENTS

| | | | |
|---|---|---|---|
| 5,592,840 | A * | 1/1997 | Miyasaka |
| 6,544,260 | B1 | 4/2003 | Kitamura et al. |
| 6,544,360 | B1 | 4/2003 | Kitamura et al. |
| 2004/0206421 | A1 | 10/2004 | Kleff et al. |
| 2006/0048867 | A1 | 3/2006 | Minchara et al. |
| 2008/0184833 | A1 | 8/2008 | Dohmann |
| 2010/0064835 | A1 | 3/2010 | Luckett |
| 2015/0211621 | A1 | 7/2015 | Sandner et al. |
| 2016/0298203 | A1 | 10/2016 | Hackel |

FOREIGN PATENT DOCUMENTS

| | | |
|---|---|---|
| DE | 69312807 T2 | 1/1998 |
| DE | 10140444 A1 | 2/2003 |
| DE | 102011055104 A1 | 5/2013 |
| DE | 102012100279 A1 | 7/2013 |
| DE | 112006000619 B4 | 2/2014 |
| DE | 102012107501 A1 | 5/2014 |
| DE | 102013218413 A1 | 3/2015 |
| DE | 102014225995 A1 | 7/2015 |
| DE | 102014105780 A1 | 10/2015 |
| EP | 1640467 B1 | 3/2006 |
| JP | H02247020 A | 10/1990 |
| JP | 2007224353 A | 9/2007 |
| JP | 2013241961 A | 12/2013 |
| RU | 2156683 C1 | 9/2000 |
| RU | 2224154 C1 | 2/2004 |
| RU | 2509242 C2 | 3/2011 |
| RU | 2449878 C2 | 5/2012 |

OTHER PUBLICATIONS

NPL: On-line translation of JP 2013241961 A1, Dec. 2013 (Year: 2013).*

Molzen M S et al: "Shot Peening and Heat Treatment Reduce Stress", Welding Journal, Americam Welding Society, Miami, FL, US, vol. 80, No. 1, p. 38-42 , p. 40, col. 2, Para. 2-4, Fig. 2, Jan. 2001.

International Search Report of PCT/DE2017/000316, dated Mar. 26, 2018.

Dirk M. Schibisch, Martin Broecking, Induktives Haerten von Lenkstangen fuer Elektolenkungen, Elektowaerme International, vol. 2, 2013 (English Abstract on p. 57).

* cited by examiner

METHOD FOR MACHINING A RACK AND RACK MACHINED ACCORDING TO SAID METHOD

BACKGROUND OF THE INVENTION

(1) Field of the Invention

The invention relates to a method for machining a rack and a rack machined according to the method, for use for example in steering systems of vehicles as so-called steering rack. The invention is also applicable to racks of other systems.

(2) Description of Related Art

Such racks are made primarily of bar steels and include at least one of the operations, such as cutting a so-called short piece to length, placing teeth in one section, hardening, straightening, end machining of ends, grinding, finishing, crack testing, washing, to provide the racks for installation in a steering system or in another system.

In the manufacture of motor vehicles, a low weight and an increased fatigue strength in terms of fuel economy and safety as well as a largely uniform stress distribution in the rack workpiece are required for each installed part as well as for a steering rack.

According to the experience in the technical field, a disadvantageous and undefinable profile of compressive and tensile stresses is present at least in the section of the gear teeth after placing the teeth, and after hardening and straightening of racks. The practitioner also refers to this effect as "chaotic" stress profile, to which reference will be made in the following in the context of the invention.

DE 102012100279 A1 and DE 102014105780 A1 describe steering racks, which supposedly have a largely uniform stress distribution in the workpiece following the operations, such as deformation and heat treatment or gear cutting and straightening before the installation. Such racks were machined with an adapted device for induction hardening to achieve a uniform hardening zone, or subjected to parameterization during the straightening process.

The presently required parameters of a uniform stress distribution in the rack work piece can thereby not be fulfilled.

Other solutions for machining generic racks concerning the problem of controlling stress states show the following:

DE 69312807 T2 discloses a conventional method for producing a steering rack for use in motor vehicles by milling a part of a cylindrical bar into a semi-cylindrical shape with a flat surface and further milling a flat section to form on its surface the rack. Such racks do not meet the current requirements because of their heavy weight and high cost. Particularly disadvantageous is milling of a portion of the surface of the steering rack which destroys the microstructure.

To produce racks simpler and cheaper, tubes with smaller wall thicknesses were used, causing problems with their strength. These problems are supposedly solved according to JP 2247020.

Thus, according to DE 69312807 T2, racks were produced with considerable technical complexity from a metal tube by in a first step, applying pressure to produce a cross-section on which the racks are to be formed,
in a second step, mounting the tube between tools that have a complementary relationship to the racks, and pressing a mandrel with a semicircular cross section into the bore of the metal tube, and
in a further step, inserting a core bar into one end of the metal tube and using an extruder to extrude the tube around the core bar in order to reduce the wall thickness of the tube.

DE 112006000619 B4 discloses a steering rack for a vehicle rack and pinion steering system having gear teeth and a shaft having a constant outside diameter and a constant wall thickness over most of its length. For this purpose, the machining process includes a forging operation on a tubular part, wherein an elongated part is inserted into the bore of a first region of the tubular part. The forging process forms the gear teeth on the first area, thereby holding the elongated part in the tubular part. Before the forging process, the tubular part is produced by performing a molding operation on a tube piece such that the outer diameter of the first region is smaller than the constant outer diameter of the shaft and the wall thickness of the first region is greater than the constant wall thickness of the shaft. The first portion is axially compressed in a kneading operation, and the elongated member is inserted into the bore of the tubular member prior to the kneading operation. The first area is kneaded onto the elongated part. During the kneading operation, the first portion is kneaded onto a removable and reusable kneading spindle, whereby the outer diameter is reduced over the length of the tube piece by the molding operation.

Despite the possible reduction of the outside diameter, the technical pursuit of this teaching would require significant technological costs.

Overall, these solutions give a skilled artisan no guidance for conquering the problem of "chaotic" or adverse stress states in a technologically advantageous manner.

In the document "Inductive hardening of steering rods for electric power steering systems" it has been reported that while the demands on the fatigue life and wear characteristics of workpieces may increase, the size and weight of the components is not allowed to increase for weight reasons. Accordingly, inductive hardening of locations of racks and the use of correspondingly high-quality, inductively heat-treated starting material should make it possible to meet these requirements (authors Dipl.-industrial engineer, Dirk M. Schibisch, Dipl.-Ing. Martin Bröcking, elektrowärme international 3-2013).

DE 102012107501 A1 describes another solution for avoiding the stress peaks and cross-sectional changes generated by deformation in a rack for a steering gear. Accordingly, the rack and a driving steering pinion are arranged so as to produce a pre-stress of the pressure piece on the rack. Although improved damping properties in terms of lower noise generation are thus achieved, the skilled artisan receives no guidance for attaining a uniform stress distribution in the workpiece.

Other documents, for example, EP 1 640 467 B1, suggest to the skilled artisan that increased strength requirements for racks such as steering racks can be achieved by changes in the microstructure. Accordingly, these have in their material microstructure 0.50 to 0.60% by weight carbon, 0.05 to 0.5% by weight silicon, 0.2 to 1.5% by weight manganese, 0.0005 to 0.003% by weight boron, 0.005 to 0.05% by weight titanium, 0.0005 to 0.1% by weight aluminum and 0.002 to 0.2% by weight nitrogen, and a residue formed by iron and incidental impurities. Such steel rods for racks are typically quenched and tempered so that they are provided with a tempered bainitic structure and a tempered martensitic structure at certain depths at least in one section of the steel rod. These structures are a prerequisite for intentional minimization of the diameter of a rack. However, such a potential for weight saving by way of minimization of the diameter cannot be fully taken advantage of after adding the gear teeth in order to solve the problem of the "chaotic" stress profile in the gear teeth with stress peaks, without any changes in the microstructure.

AT 515352 A1 (DE 102014225995 A1) describes a sintered component with gear teeth, which includes teeth with tooth roots and tooth flanks. All teeth and tooth roots of the gear teeth have a plasma-nitrided or plasma-nitrocarburized layer and the tooth roots have a permanent tooth root strength of at least 200 MPa according to DIN 3990. The method for producing this sintered component includes the steps of powder pressing, sintering and hardening. Although a high tooth root strength can be achieved even with such sintered components, the tooth flanks can have a maximum value of the compressive inherent stresses in a range from 200 MPa to 1500 MPa, a further improvement of the fatigue strength of the sintered component can be achieved, and the risk of cracking in the area of the teeth can be reduced and these sintered components can be implemented as a rack with straight gear teeth or helical gear teeth, the skilled person can therefrom not obtain any suggestion for solving the problem of stress states when machining generic racks. The technology disclosed therein is focused on plasma nitriding or plasma-nitrocarburizing for hardening sintered components, in order to avoid for example process-related distortions.

It is known to those skilled in the art that workpiece surfaces may be reworked to either eliminate adverse inherent tensile stresses or to introduce beneficial compressive stresses into the critical parts by mechanical and thermal means, such as shot peening or induction annealing mentioned above. Thus, material states near the surface, such as inherent stress or solidification, can be modified. Shot peening is primarily used to increase the surface strength of workpieces.

US 2006/0048867 A1 suggests to counteract the stress cracks caused by inherent stresses in steels treated by hardening by irradiating such surfaces radiographically during a treatment with a gas beam so as to measure the formation of optional or desired inherent stresses. However, this teaching is based on technologically induced changes in the microstructure.

DE 102013218413 A1 discloses to preheat a trailing arm and a torsion bar immediately before welding to a temperature between 120 and 150° C., wherein trailing arm and torsion bar are subjected to shot peening after welding. Shot peening is supposed to increase the durability in service.

U.S. Pat. No. 6,544,360 B1 discloses a surface treatment process for producing motor vehicle springs according to DE 102013218413 A1, by which a correspondingly treated surface exhibits a better stress profile when the motor vehicle springs are heated and then treated with shot peening in order to achieve desired inherent compressive stresses at the surface. Accordingly, a method for shot peening of metal components, in particular of a motor vehicle stabilizer, is proposed which is characterized by the method steps providing a metal component and inserting the metal component into a blasting system, wherein the metal component is heated before the blasting process,
 cleaning with a definable cleaning beam velocity, and
 subsequent shot peening with a definable shot peening beam velocity, wherein the shot peening beam velocity is greater than the cleaning beam velocity. Since blasting is controlled by the velocity, the dimension of solidification is not always definable.

From the expert point of view, it may be added that uneven hardening zones and uneven stresses within the workpiece to be hardened can be kept small with progressive hardening according to DE 102012100279 A1 cited above. The adaptation of the cross-sectional shape of an inductor to the cross-sectional shape of the rack to be hardened produces hardness zones which have a flat interface with the non-hardened region. This flat interface is supposed to cause a uniform stress distribution in the workpiece, whereby the rack can attain high mechanical stability, however this is associated with relatively high costs.

A combination of both methods would therefore also not be able to adequately or completely solve the problem of "chaotic" inherent stress with stress peaks in the gear teeth.

On the other hand, DE 10140444 A1 rejects subsequent shot peening for increasing the dynamic load capacity of a toothed component in order to be able to increase the tooth flank carrying capacity in the area of the tooth root.

After evaluating these measures that have other approaches and goals than the problems to be solved here, which at best represent individual solutions, the skilled artisan receives no suggestions for controlling the "chaotic" stress distribution previously addressed in the manufacture of steering racks in a targeted or definable manner. He is not even certain, that the result achievable with a blasting treatment including shot peening can also adversely affect the workpiece, especially if the blasting treatment is not controllable.

Also, other considerations of methods in other fields, as described for example in DE 19500078 A1, offer no solutions. This method relates to the reduction of the relative breaking torque in the region of predetermined breaking points of components by means of cold deformation by shot peening. Although it is assumed here that components subjected to bending or torsion have stress peaks at cross-sectional transitions, which could lead to breaks without appropriate countermeasures on the material side, this solution would not be transferable to the racks considered here.

The skilled artisan recognizes that more complex considerations are required because permissible or required stress distributions cannot be controlled technologically within the scope of normal work processes. This requires creative considerations in order to be able to successfully integrate shot peening, which was previously considered only as post-treatment, into the work processes for producing racks or to combine this with the measures analyzed above or with other measures. Because the analysis of the prior art also shows that the experience gained in the practice of producing steering racks cannot be replaced by purely computationally determined technologies. Furthermore, a progressive measure of "trial and error" is required.

Although an early source by Neuber (Research in Engineering, Vol. 29 (1963)) teaches with respect to the stress distribution in racks that exact stress functions can be obtained with the help of complex computational methods, which can lead to new computational foundations for the stress distribution in racks with arbitrary profile and arbitrary force application. However, the skilled artisan seeking new computational foundations for practical applications does not find corresponding solutions.

By examining at the aforementioned solutions in the prior art, no solution can be combined which avoids the disadvantageous, undefinable or uneven "chaotic" stress states, in particular the disadvantageous tensile stresses and their stress peaks, which are present in the gear teeth after hardening and straightening a rack. Thus, optimizations of the mass and material necessary to avoid later cracks or fractures of a rack cannot be readily realized.

Accordingly, a new solution must be found that
meets the requirements of weight savings in racks by minimizing the rack diameter and thus also the enveloping circle diameter of the gear teeth with a largely uniform stress distribution and without changes in the microstructure,
avoids the disadvantage of a decreasing fatigue strength of the rack and the formation of cracks or fractures, and
creates a potential for diameter minimization.

BRIEF SUMMARY OF THE INVENTION

The object of the invention is to convert the stress system with a chaotic inherent stress profile of tensile and compressive stresses that is present after hardening and/or straightening of the rack by way of partially known technologies and operations in a combined sequence of machining operations into a stress system that optimizes the strength and the use of materials as well as the diameter of the rack, without changing or destroying the microstructural components of the respective steel.

In this context
X-ray tests, as known in the art and specifically applied, e.g. according to US 2006/0048867 A1, and/or
the well-known shot peening, previously considered only as post-treatment or applied after a technological waiting period to avoid crack formation, in metal components (e.g., as described above in DE 102013218413 A1, DE 102011 055104 B4, DE 10140444 A1) for introducing compressive stresses
should be integrated into a continuous sequence of operations as well as selectively used with a functionally combined new effect of a more uniform distribution of stress in the workpiece.

The inventive principle of the method for machining a rack produced from a metallic material, wherein after hardening, or after hardening and straightening, initially a "chaotic" inherent stress profile of tensile stresses and compressive stresses is present at least in the region of a gear teeth, is that the inherent stress profile is converted by a functionally combined series of steps of a machining sequence into a permissible inherent stress profile without causing changes in the microstructure, whereby at least the region of the gear teeth receives a pre-stress with defined introduced inherent compressive stresses without tensile stresses, so that a physical system with stress values of inherent compressive stresses and the permissible inherent stress profile of a substantially uniform stress distribution or stress plane is present in the region of the gear teeth.

Compared to the above-evaluated AT 515352 A1 (DE 102014225995 A1), according to which for a sintered component with gear teeth a maximum value of inherent compressive stresses for improving the fatigue strength of the sintered component is possible, the control of stress states is according to the invention achieved without changing the microstructure of the steel, so that the present technology is different therefrom both in principle and qualitatively.

For this purpose, after hardening, or after hardening and straightening, measured values of axial and transverse stresses representing tensile stresses in an axial direction and compressive stresses in a transverse direction occurring in selected sections of the gear teeth in at least one rack are used for the definition of the "chaotic" stress profile as a reference profile or a theoretically assumed stress profile for lots or series of racks to be machined according to the invention with the same parameters, namely in the context of a technological preparation of the respective lots or series.

The method takes into account that a generic rack normally has the stress system referred to here as "chaotic" following the basic operations, such as cutting short pieces, applying teeth in a section, hardening, straightening and before finishing the end faces, grinding, finishing, crack testing and washing. The person skilled in the art has recognized the tensile and compressive stresses prevailing in a toothed rack after application of the gear teeth and hardening, in order to be able to determine their extent, namely non-destructively by means of X-ray diffraction measurements of the inherent stresses. The inherent stresses are measured in at least one near-surface layer of the sections of the gear teeth in their axial direction and transverse direction to a depth of <100 μm.

Since the radiographic stress is measured by determining the lattice expansion in a crystalline lattice as a result of inherent stresses, a measurement is to be performed depending on a coordinate system, wherein the stresses are determined from a multiaxial stress state.

The toothed region requires a special setting of the X-ray apparatus, such as a diffractometer, on the workpiece and the material, including criteria such as
the choice of the areas to be irradiated, and
the determination of the measurements concerning the measuring positions, such as interference lines, angular ranges, tilting.

Consequently, for the X-ray diffraction measurements of the inherent stresses, the selected (boundary layer) sections of the gear teeth are determined in order to be able to detect in their axial direction and transverse direction the existing compressive and tensile stresses as measured values of axial and transverse stresses.

Although X-ray diffraction measurements in workpieces are generally known, as mentioned above in relation to US 2006/0048867 A1, it should be emphasized that for the racks in the present disclosure the first machining step must be provided for the following measures beyond normal action by a skilled artisan in order to ultimately achieve usable results for the desired largely uniform stress distribution without changes in the microstructure. The aimed uniform stress distribution according to the invention is achieved not only without changes in the microstructure, but also without additional means (such as additional gas beam treatment according to US 2006/0048867 A). Thus, particularly structured X-ray diffraction measurements of the inherent stresses according to the invention are integrated into a technological process having a synergetic effect.

Since the compressive and tensile stresses observed in the present "chaotic" stress system are now measurable and detectable, stress peaks of the tensile stresses can be theoretically determined or assumed, which can be functionally integrated into the machining operation. On the other hand, it makes technological sense, because a single "representative sample" can be assumed, i.e. without having to perform measurements of the "chaotic" stress system on each rack of the lots or the series. For example, of the tensile stresses and compressive stresses measured in the range of ±<2.0 MPa×$10^3$, at least ±0.5 MPa×$10^3$ can be defined as stress peaks or amplitudes.

This measure according to the invention of a first technological step already characterizes the particular inventive aspect, which goes beyond the initially ascertained state of the art, within the functionally based machining operation, namely with regard to the uniform stress distribution desired in the gear teeth without changes in the microstructure.

Accordingly, the aforementioned stress peaks of tensile stresses are eliminated, smoothed or reduced by introducing near-surface inherent compressive stresses by way of shot peening, for example, using glass-bead beams, which can be carried out for a brief time of <10 s.

Alternatively, the stress peaks of tensile stresses can be eliminated, smoothed or reduced by inductive heating such as stress relieving, wherein heating can be carried out in the range of 120 to 160° C. and values according to the respective stress states can be detected before heating and after heating.

The inductive relaxation can be carried out depending on the type of gear teeth, wherein a uniform or variable gear teeth or the characteristic of the material can be taken into account.

After shot peening or inductive heating and elimination, smoothing or reduction of the stress peaks or amplitudes, the region of the gear teeth receives the pre-stress with the defined introduced compressive inherent stresses without tensile stresses by way of subsequent steel wire shot blasting (or grit blasting as well as steel shot peening), so that the desired or permissible inherent stress profile is achieved.

For this purpose, the specifically prescribed values of inherent compressive stresses are introduced by means of beam pressure in the ranges of ±p1.

An inventive feature of the application of this cut steel wire blasting is that the compressive stresses are intentionally defined depending on the previously measured values and applied in functional synergy with the prior elimination, smoothing or reduction of the stress peaks or amplitudes. At the same time, the deformation caused by the blasting process can at the same time be determined and controlled in a defined sample by determining the compressive stresses as a measured intensity by means of the Almen intensity measurement, hereinafter also referred to as Almen test. Among other things, the hardness and shape of the blasting material, the angle of incidence, the kinetic energy of the blasting material and any obstructions can be taken into account. The Almen test thus becomes a technologically integrated component of the functionally combined series of steps of the machining operation according to the invention. Therefore, a single rack can represent the defined sample as Almen test sample for the predetermined duration or for a predetermined number of lots or series.

By virtue of the effective intimate connection and mutually supportive combination of these process steps in the machining operation according to the invention, the stress peaks detected in the physical stress system of the microstructure can be converted into a uniform stress plane or stress distribution with the surprising effect that a pre-stress of the gear teeth in form of compressive inherent stresses is present in the particular section of the gear teeth.

With the invention, disadvantageous features of a variable gear teeth compared to a constant gear teeth can be taken into account by detecting and covering for variable gear teeth the different tooth root radii and different angles of the tooth flanks with the method according to the invention. Thus, the original inherent stress profile of tensile stresses and compressive stresses can be converted into a permissible inherent stress profile, taking into account the type of gear teeth or the characteristic of a material of the rack.

The dimension of a diameter of the rack can thus be optimized, especially as steering racks of vehicles compared to others with comparable axle loads.

The method allows values of inherent compressive stresses in the gear teeth in the range of >−0.6 MPa×10$^3$ to <2.0 MPa×10$^3$, such that these values are ultimately a qualitatively new characteristic of racks machined according to the method.

The steering rack produced by the method according to the invention therefore has in the section of the gear teeth
  a) the compressive stresses introduced into the gear teeth,
  b) the physical stress system forming a uniform stress plane/distribution, and
  c) the pre-stress converted by inherent compressive stresses of the gear teeth in the dimensions,
which properties give the steering rack a new, functionally uniformly combined quality. Thus, the increasing demands for weight savings by minimizing the rack diameter and thus also the enveloping circle diameter of the gear teeth can be met, the fatigue strength can be increased despite minimizing the diameter, and for automotive steering systems the demand for higher axle loads of the vehicles can be met, and the technological costs can be kept low.

BRIEF DESCRIPTION OF THE DRAWINGS

The drawings show in

FIG. 2.1 the diagram of a measured stress profile σ of tensile stresses σ+ and compressive stresses σ− in the gear teeth 2 according to FIG. 1 after hardening and straightening with identification of stress peaks σ+$_{peak}$ of the tensile stresses σ+ and stress peaks σ−$_{peak}$ of the compressive stresses σ− in the rack 1 of FIG. 1, which is used as a basis as designated "σ-profile" of a selected sample of the rack 1 for lots or series of racks 1 to be machined according to the invention with identical parameters as a reference stress profile σ or as a theoretically assumed stress profile σ of the lots or series of racks 1 having the same parameter;

FIG. 2.2 the diagram "σ-profile" of tensile stresses σ+ and compressive stresses σ− in the gear teeth 2 of the rack 1 according to FIG. 1 after inventive elimination or smoothing of stress peaks σ+$_{peak}$ of the tensile stresses σ+, here referred to as "stress peak smoothing";

FIG. 2.3 the diagram of a permissible or predetermined stress profile σ$_{perm}$ of compressive stresses σ− in the gear teeth 2 of the rack 1 according to FIG. 1 according to the invention following a machining operation according to the invention, whereby the "σ-profile" in accordance with FIG. 2.1 was converted into a permissible, not designated stress profile σ$_{perm}$ and the region of the gear teeth 2 has a pre-stress with intentionally introduced, not designated inherent compressive stresses σ−$_E$ without tensile stresses σ+, here symbolically indicated with arrows, according to which
  in a first stage, designated as "Process I", the functionally combined series of steps of a machining operation intentionally smoothed, reduced or eliminated the not designated stress peaks σ+$_{peak}$ of the tensile stresses σ+ of FIG. 1 by introducing near-surface, not designated inherent compressive stresses σ-$_E$ by way of shot peening, and in a second stage, designated as "Process II", as a conclusion in the functionally combined series of steps of the machining operation according to the invention following the shot peening or inductive heating and eliminating, smoothing or reducing these stress peaks σ+$_{peak}$ the allowable inherent stress σ$_{perm}$ is achieved by a subsequent steel wire shot blasting according to a designated "σ-specification";

Exemplary embodiments of the invention will be explained in more detail below.

DESCRIPTION OF THE INVENTION

Figure 1:
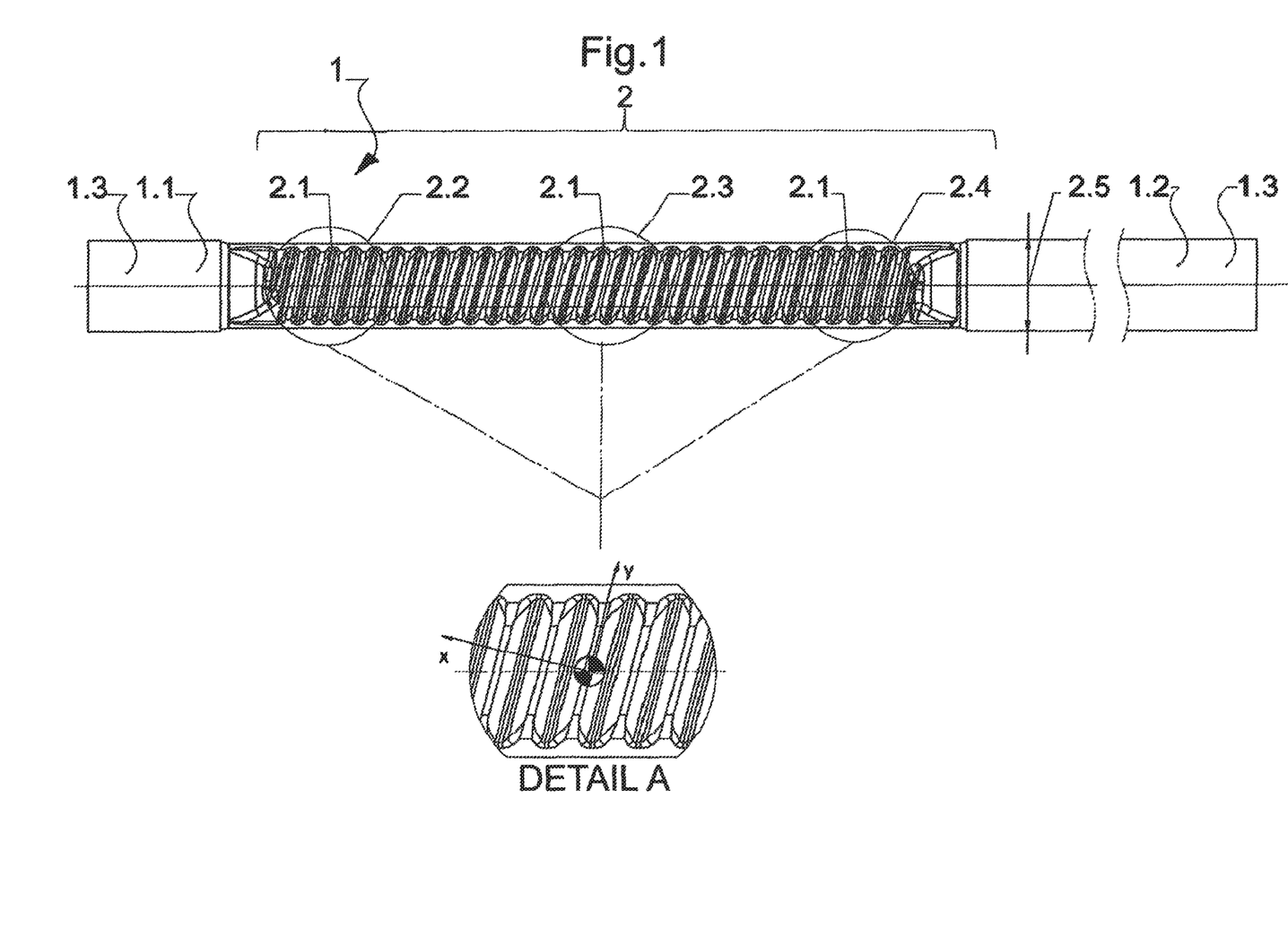
FIG. 1 a plan view of a rack 1 to be machined according to the invention, shown as a steering rack with a measuring range that is split in a
  Section 2.2 of the gear teeth 2, defined up to the 5th tooth starting from a pin 1.1,
  Section 2.3 of the gear teeth 2, defined as the measuring range center, and
  Section 2.4 of the gear teeth 2, defined up to the 5th tooth starting from a shaft 1.2,
and a detail A from these sections 2.2, 2.3, 2.3 of the gear teeth 2 emphasized for the purpose of illustration, in which the tensile stresses σ+ are measured in an axial direction x and the compressive stresses σ− are measured in a transverse direction y.
Figure 3:
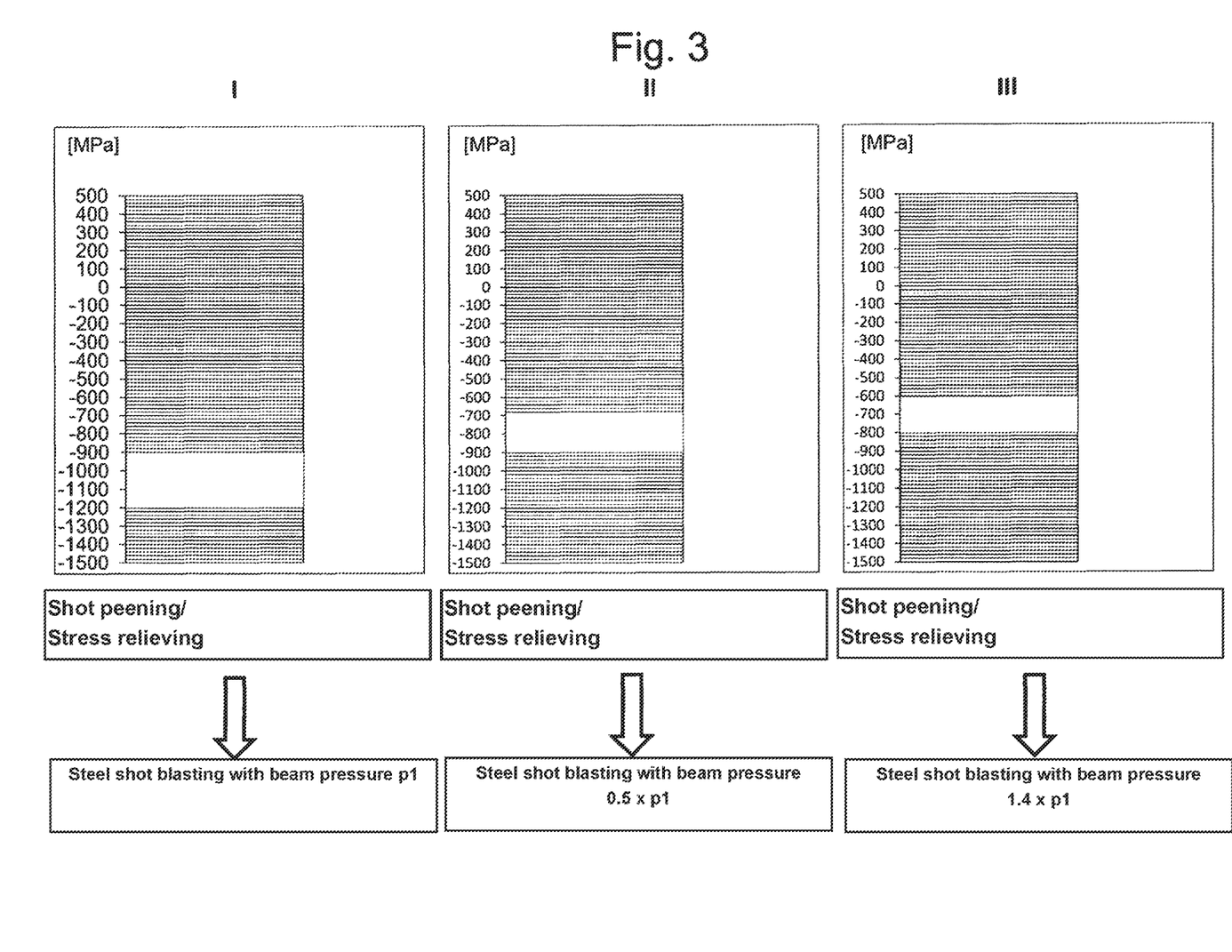
FIG. 3 three bar graphs with the measured values of inherent compressive stresses σ-$_E$ obtained in the gear teeth 2 of FIG. 1, as they were introduced according to the invention by means of shot peening or stress relieving and steel shot blasting with different beam pressures in a machining operation, namely in block diagrams designated with I, II, III.
Figure 4:
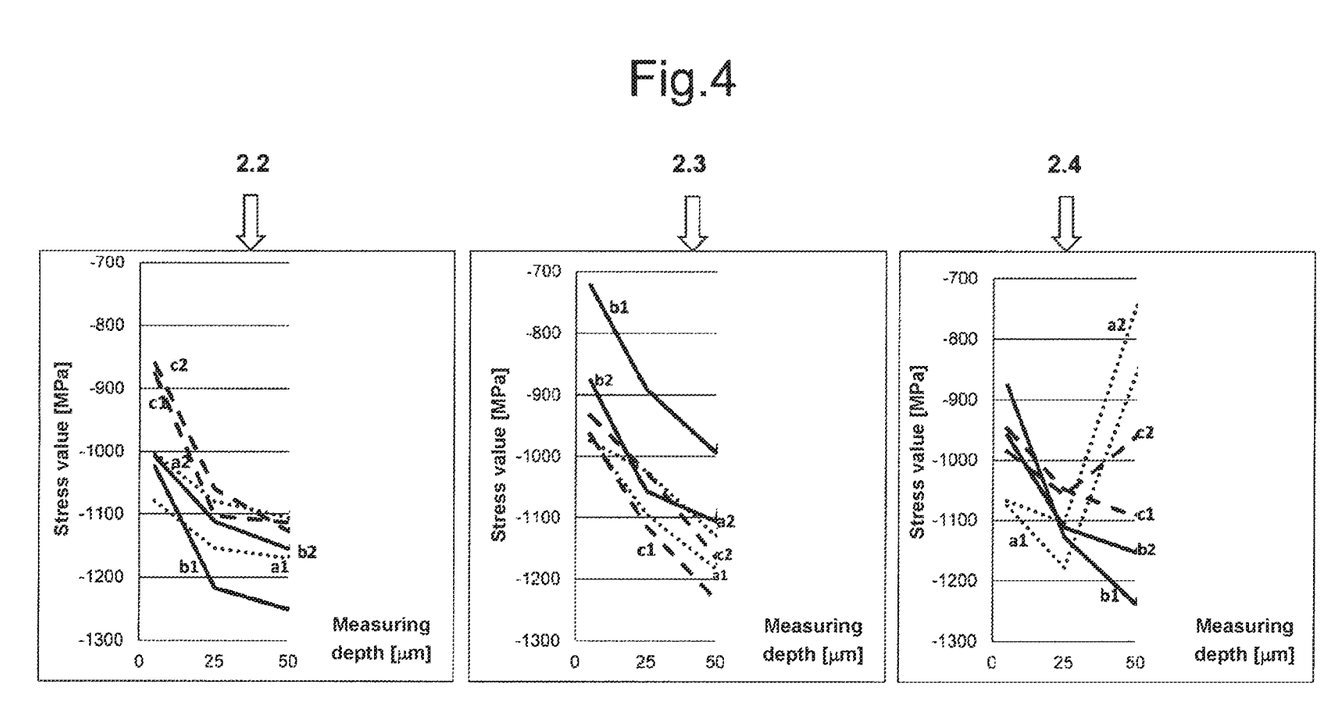
FIG. 4 an overview, depicted as diagrams, of the detailed stress values achieved in the sections 2.2, 2.3 and 2.4 of the gear teeth 2 of the toothed rack 1 according to FIG. 1.

For a better understanding of the reproducibility of a rack 1 to be machined according to the invention according to FIG. 1, technological conditions according to FIGS. 2.1, 2.2, 2.3, results according to FIG. 3, and data such as possibly mandatory data according to FIG. 4 are shown for the examples.

In FIG. 1, a rack 1 is used as a basis, having gear teeth 2 with teeth 1 introduced between pin 1.1 and shaft 1.2 by non-cutting shaping, by end faces 1.3 of limited length and a diameter 2.5, which is to be machined according to the invention after hardening and straightening.

Figure 21:
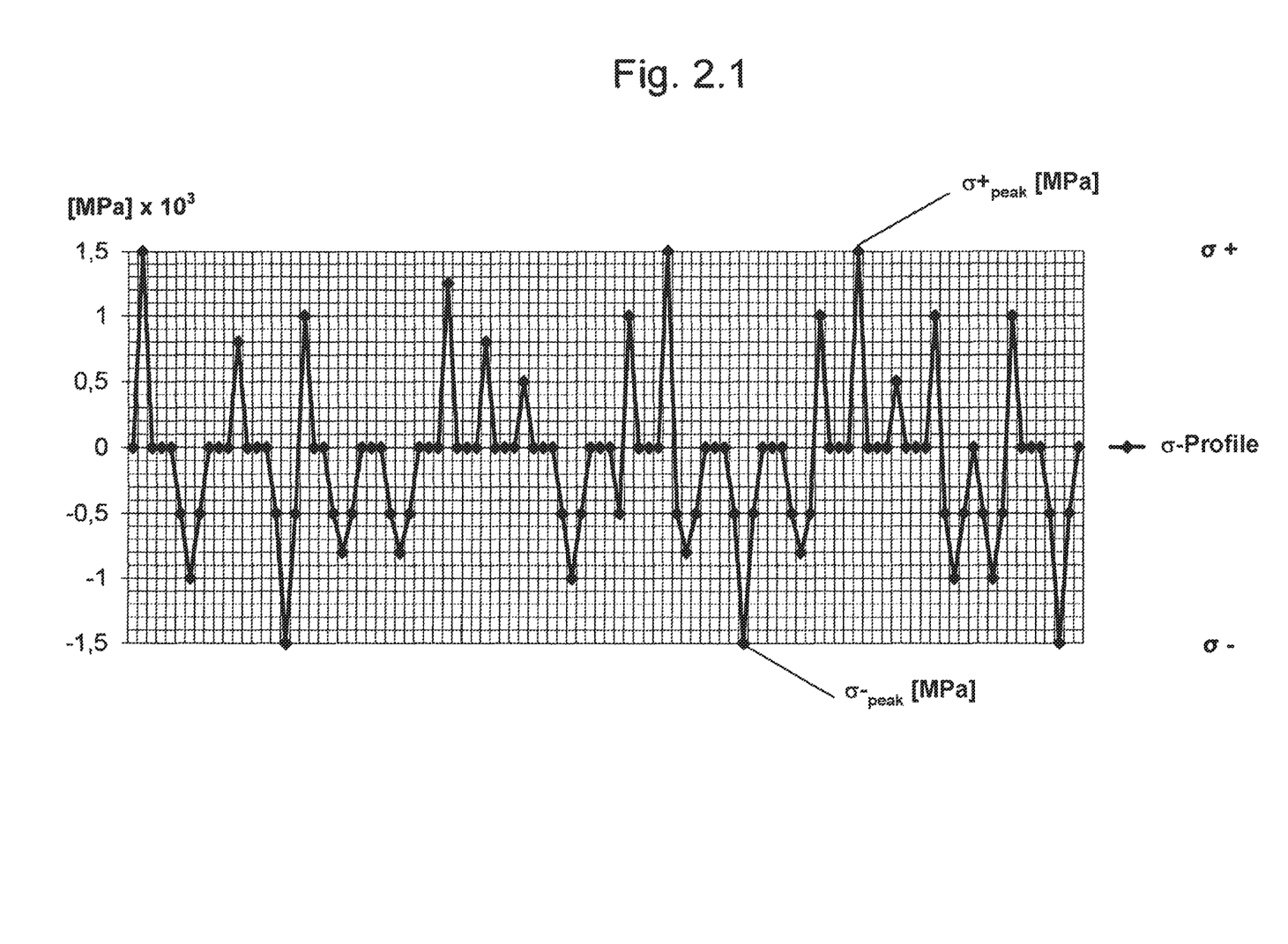

In view of the problem initially analyzed, namely that after hardening and straightening of the rack 1, disadvantageous, undefinable or uneven stress states, here referred to as "chaotic", are present in the gear teeth 2, with a stress profile σ, as shown in FIG. 2.1, of tensile stresses σ+ and compressive stresses σ– in the gear teeth 2 with particularly disadvantageous tensile stresses σ+ and their stress peaks σ-$_{peak}$, and externally specified mandatory data, optimizations of the mass and material use while avoiding later cracks or breaks of the rack 1 are required, the rack 1 must be processed so as to meet the requirements for weight saving by minimizing the rack diameter and thus also the envelope diameter of the gear teeth with a largely uniform stress distribution and without change in the microstructure, avoid the disadvantage of a decreasing fatigue strength of the rack and the formation of cracks or fractures, and offer at all a potential for diameter minimization.

The following symbols designate consistently:

σ+ a tensile stress,

σ– a compressive stress,

σ-$_E$ a compressive inherent stress,

σ a stress profile, also "chaotic" as a (inherent) stress profile, and

σ$_{perm}$ a permissible, desired, given or achieved (inherent) stress profile.

According to the invention, in a functionally combined sequence of steps of a machining operation, the (inherent) stress profile σ which is disadvantageous for satisfying the required parameters is to be converted into an allowable (inherent) stress profile σ$_{perm}$ without changing the microstructure, wherein (at least) the region of the gear teeth 2 receives a pre-stress with defined introduced inherent compressive stresses σ-$_E$ without tensile stresses σ+, so that as a result of the machining a physical system with stress values of inherent compressive stresses σ-$_E$ and the permissible (inherent) stress profile σ$_{perm}$ of a largely uniform stress distribution or stress plane is present in the region of the gear teeth 2.

The machining method according to the invention is based on the fact that in the gear teeth 2 with teeth 1 necessarily, i.e. measured or not measured or detected or not found, a "chaotic" (inherent) stress profile σ of tensile stresses σ+ and compressive stresses σ– according to FIG. 2.1 is present. In the context of the invention, this state is to be examined and defined on a sample of the rack 1 as follows. As an important aspect of the invention and as a quasi-technological preparation of the rack 1 according to FIG. 1 to be machined with these integrated steps, the section of the gear teeth 2 with the teeth 2.1 (=length of the gear teeth 2) is each divided into a section 2.2 as a measuring range up to the 5th tooth 2.1 starting from the pin 1.1, a section 2.3 as a measuring range center, and a section 2.4 as a measuring range up to the 5th tooth starting from the shaft 1.2.

To this end, the emphasized detail A of the gear teeth 2 shows symbolic vector arrows for the measurement of tensile stresses σ+ in an axial direction x, and for the measurement of compressive stresses σ– in a transverse direction y.

On the basis of this technological system prepared for the inventive machining, the tensile stresses σ+ of the gear teeth 2 in the axial direction x and the compressive stresses σ– in the transverse direction y are detected in the selected (near-surface) areas by X-ray diffraction measurements and recorded as measured values.

Although X-ray diffraction measurements in workpieces are generally known, it should be emphasized that in the case of the present rack 1 measures had already to be developed and tested for the first technological approach that went beyond the actions expected from a skilled artisan, in order to ultimately attain a largely uniform stress distribution and usable results without changes in the microstructure. Since the X-ray diffraction measurement are performed by determining the lattice expansion as a result of inherent stresses in a crystalline lattice, a measurement could be carried out in the defined coordinate system, whereby the stresses are determined from the multiaxial stress state.

Since the gear teeth 2 requires a special adjustment of the X-ray apparatus, for example a diffractometer, on the rack 1, the following criteria must be observed:

the choice of areas to be irradiated, and the determination of the measurements concerning the measuring positions, such as interference lines, angular ranges, tilting.

Accordingly, for this technologically preparatory step, the (near-surface layer) sections 2.2, 2.3, 2.4 of the gear teeth 2 to be selected for the x-ray diffraction measurements of the inherent stresses must be determined. Hereby, the present stress profile σ of tensile stresses σ+ and compressive stresses σ− in the gear teeth 2 is determined in the axial direction x and the transverse direction y after hardening and straightening with identification of stress peaks $σ+_{peak}$ of the tensile stresses σ+ and stress peaks $σ−_{peak}$ of compressive stresses σ− and recorded as measured values.

This approach according to the invention has the advantage that the "chaotic" stress profile σ of a selected sample of the rack 1 can thereafter be used in practice as a defined reference stress profile σ or as a theoretically assumed stress profile σ for the lots or series of racks 1 to be machined with identical parameters.

FIG. 2.1 shows in form of a diagram a reference stress profile σ or a theoretically assumed stress profile σ for lots or series of racks 1 with identical parameters, from which the stress profile σ and values in the dimension [MPa]×10³ of tensile stresses σ+ and compressive stresses σ− the gear teeth 2 after hardening and straightening with indicated stress peaks $σ+_{peak}$ of the tensile stresses σ+ and stress peaks $σ−_{peak}$ of the compressive stress σ− for the comparison rack 1 shown in FIG. 1 can be collected. This stress system, which has been obtained from a selected sample of the rack 1, can then be used for lots or series of racks 1 to be produced in accordance with the invention and with the same parameters as a reference stress profile or as a theoretically assumed stress profile σ with the values of tensile stresses σ+ and compressive stresses σ−.having the dimension [MPa]×10³.

Figure 22:
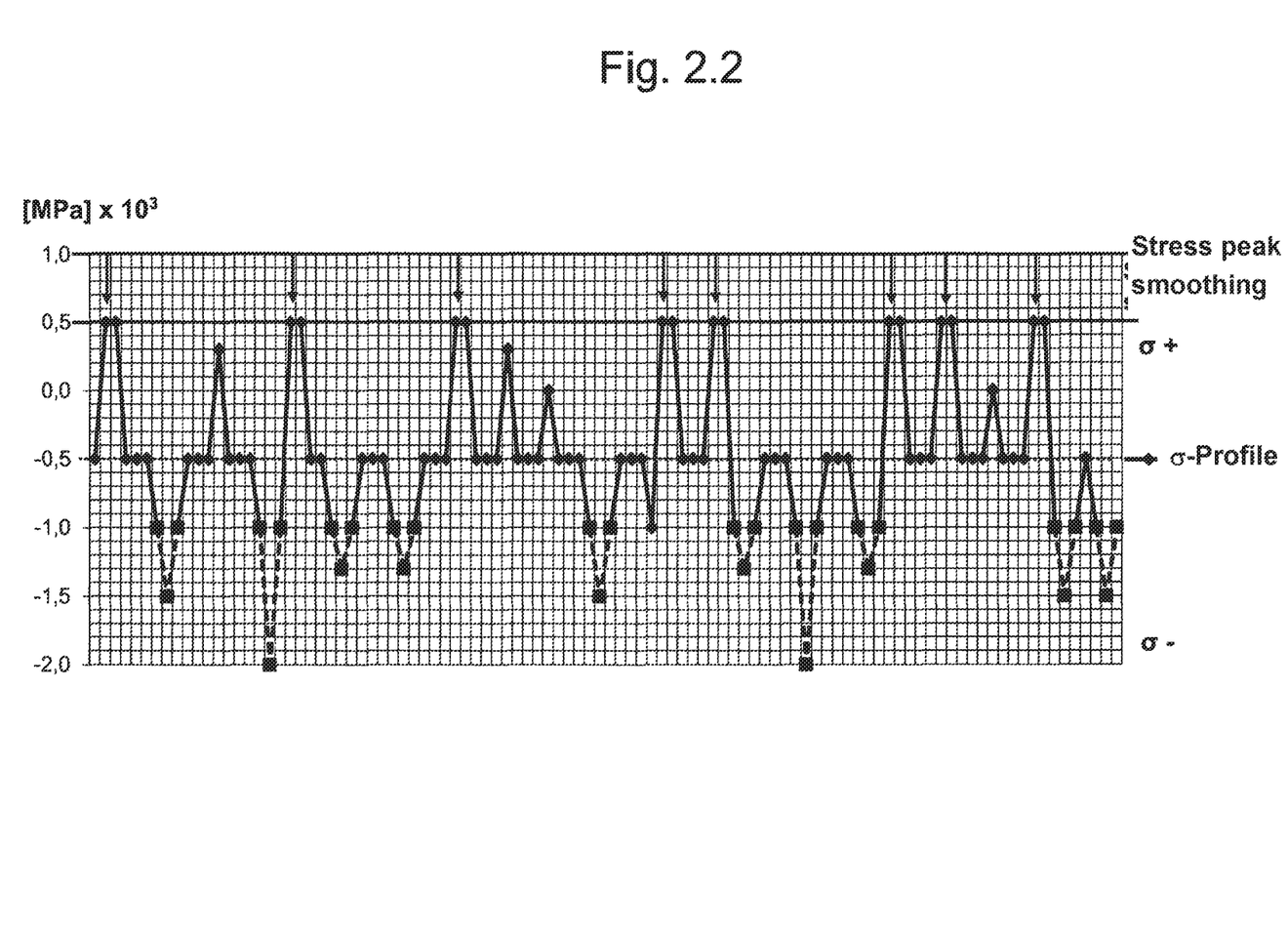
Figure 23:
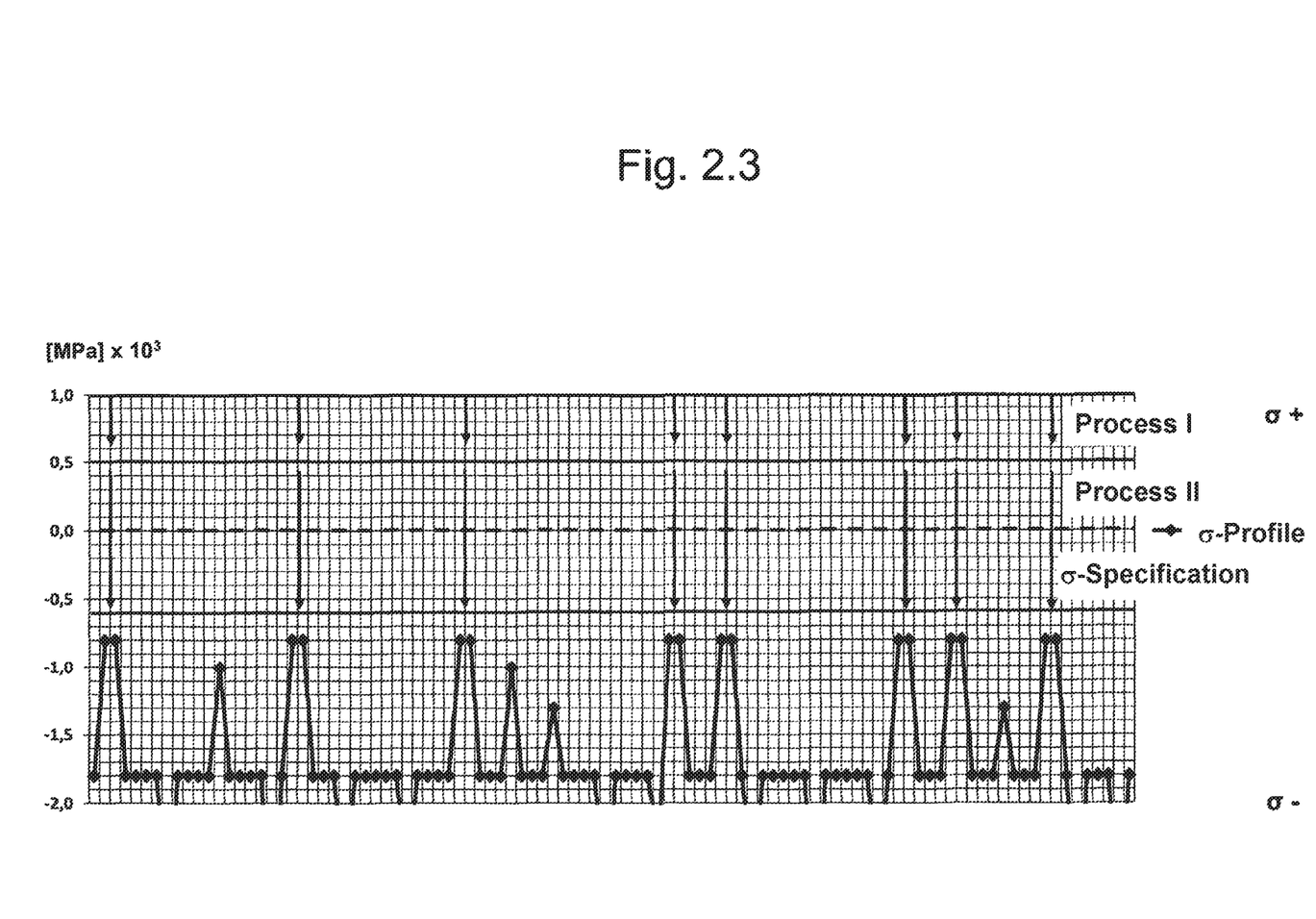

FIG. 2.2 shows schematically for the method that and how stress peaks or amplitudes $σ+_{peak}$ of the tensile stresses σ+ are present in the functional combined series of steps of a machining operation. Accordingly, the stress peaks or amplitudes $σ+_{peak}$ of tensile stresses σ+ having values with the dimension [MPa]×10³ can be defined and eliminated according to a first stage referred to as stress peak smoothing, designated in FIG. 2.3 as Process I.

Figure 5:
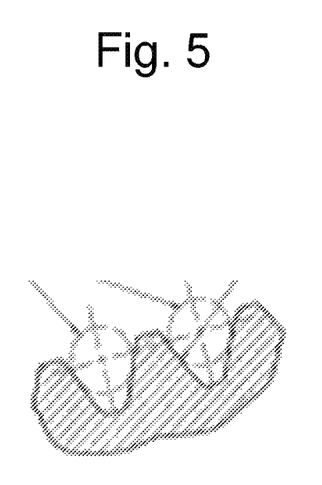
FIG. 5 a schematic diagram of the disadvantageous "failure-to-reach" the tooth base which is to be avoided when blasting with glass spheres.

The functionally combined series of steps of a machining operation includes that the stress peaks $σ+_{peak}$ of tensile stresses σ+ are smoothed, reduced or eliminated by introducing near-surface inherent compressive stresses $σ−_E$ by shot peening, such as blasting with glass beads, as symbolically indicated with arrows according to the first stage as well as in FIG. 2.3 which will be described below in more detail. Shot peening can be carried out for a brief time of <10 s. In blasting with glass beads, the spheres of the blasting material are to be sized so that a respective tooth root radius in the tooth root of the gear teeth 2 can be irradiated, in order to avoid a disadvantageous "failure-to-reach" the tooth root, as schematically illustrated in FIG. 5.

Alternatively, the stress peaks $σ+_{peak}$ of tensile stresses σ+(and possibly stress peaks $σ−_{peak}$ of compressive stresses σ−) can be eliminated, smoothed or reduced by inductive heating such as stress relieving. Heating can take place in the range from 120 to 160° C., whereby stress values can be measured before and after heating.

Accordingly, after the shot peening or stress relieving according to FIG. 2.2 (initially as a technological intermediate stage of the method according to the invention), a (inherent) stress profile σ without stress peaks $σ+_{peak}$ is attained.

According to the invention, a pre-stress with defined inherent compression stresses $σ−_E$ without tensile stresses σ+ is to be introduced in the region of the gear teeth 2 so that by looking ahead, a physical system with stress values of (inherent) compression stresses $σ−_E$ and the permissible (inherent) stress profile $σ_{perm}$ with a largely uniform stress distribution or stress plane is present in the region of the gear teeth 2. To this end, after shot peening or inductive heating and elimination, smoothing or reduction of the stress peaks $σ+_{peak}$ or amplitudes, the allowable inherent stress profile $σ_{per}$ (possibly to be achieved according to the compulsory data) is achieved by a subsequent steel wire shot blasting with a beam pressure p1, in particular in a second stage II according to FIG. 2.3 and as a conclusion within the functionally combined series of steps of the machining operation according to the invention. Thus, the pre-stress with the intentionally introduced compressive inherent stresses $σ−_E$ without tensile stresses σ+ is present in the area of the gear teeth 2, as shown in the diagram in FIG. 2.3 according to a σ-specification.

FIG. 3 shows values of desired compressive inherent stresses $σ−_E$ (and thus an inherent stress profile or $σ_{perm}$ that is permissible or obtained according to compulsory data) for processed racks 1, as were deliberately introduced by the machining operation according to the invention by shot peening or stress relieving and steel wire shot blasting at beam pressures of, for example, p1 in accordance with block diagram I, 0.5×p1 in accordance with block diagram II, or 1.4×p1 in accordance with block diagram Ill.

The steel wire operating here as strengthening beams can be controlled with regard to the specific values of inherent compressive stresses $σ−_E$ to be introduced after the "Almen test" integrated in the machining operation (with preceding paint test, if applicable) to ensure the quality. While the beam is operated, the operating pressure is controlled, and the rack 1 is available after the "Almen test" quasi as a test specimen, on which (see FIG. 4) it can be demonstrated that as a result of the steps linked with the present invention with the values a1=axial stress beginning, a2=transverse stress beginning, b1=axial stress center, b2=transverse stress center, c1=axial stress end, c2=transverse stress end, a permissible stress plane or stress distribution exists in the sections 2.1, 2.2, 2.3 of the gear teeth 2.

Since values of inherent compressive stresses $σ−_E$ in the range of, for example, >−0.6 MPa×10³ to <−2.0 MPa×10³ are possible in the sections 2.2, 2.3, 2.4 of the gear teeth 2, the invention enables the following with respect to the constructive development of racks 1:

In the conventional machining of a rack 1, the designer commonly investigated its cross-sectional behavior and optimization with respect to the rack load, a bending line for the given load case, and the dynamic fatigue tests to achieve the corresponding elastic modulus and the desired fatigue life. He determined, for example, a toothed rod diameter D of 28 mm in the region of the gear teeth 2. Although the inherent compressive stresses—$σ−_E$ or the magnitude and direction of near-surface stresses a could be disregarded, however, tensile stresses σ+ in the gear teeth 2, i.e. the negative "chaotic" stress profile σ of tensile stresses σ+ and compressive stresses σ− (see FIG. 2.1) disadvantageously remained.

The skilled artisan who now accepts the inventive teaching can advantageously deepen the structural optimization of racks 1 by     investigating factors important for fatigue strength and service life, such as cross-sectional area and section module of the teeth 2.1 at the tooth root (including tooth root radii and their corresponding notch effect) and tooth width, tooth root plane or surface,     furthermore converting the inherent stress profile σ of tensile stresses σ+ and compressive stresses σ− as a function of a variable gear teeth 2 $i_{var}$ or constant gear teeth 2 $i_{constant}$ or as a function of the characteristic of a material of the rack 1 into the permissible inherent stress profile $\sigma_{perm}$, eliminating the tensile stresses σ+ through intentional introduction of near-surface inherent compressive stresses $\sigma-_E$ (e.g. 0.02 mm below the surface) and minimizing the diameter D of the racks 1 to, for example, 26 mm, and even optimizing the dimensioning of the diameter D of the rack 1, such as the steering rack of a vehicle, with the same axle loads of a vehicle.

This is possible because the method according invention provides a rack 1 which allows values of compressive inherent stresses $\sigma-_E$ in the range of >−0.6 MPa×10³ to <−2.0 MPa×10³.

FIG. 4 shows how the stress ratios which originally act unfavorable in the physical stress system of the microstructure, were converted as a result of the steps associated with the invention with the above defined values a1, a2; b1, b2; c1, c2 into a permissible stress plane or stress distribution in the sections 2.2, as measured on the 5th tooth starting from the pin 1.1,
2.3, in the measuring range center,
2.4, as measured on the 5th tooth starting from the shaft 1.2 of the gear teeth 2. Thus, default values such as external compulsory data can be compared to the achieved actual values and confirmed to be satisfied, namely that an advantageous pre-stress from inherent compressive stresses—$\sigma-_E$ without detrimental tensile stresses σ+ is present in the gear teeth 2.

The invention is technologically applicable with relatively low costs and makes it possible to meet the demand for saving weight of racks by minimizing the rack diameter. The durability of racks is satisfied, and cracks or breaks in the gear teeth are avoided. In particular, in automotive steering systems, the demand for higher axle loads of vehicles can be realized.

LIST OF REFERENCE NUMERALS AND SYMBOLS USED

1=rack
1.1=pin
1.2=shaft
1.3=front side
2=gear teeth
2.1=tooth
2.2=section of the gear teeth 2 as a measuring range starting from the pin 1.1
2.3=section of the gear teeth as measuring range center
2.4=section of the gear teeth 2 as a measuring range starting from the shaft 1.2
2.5=diameter of the rack 1
x=axial direction
y=transverse direction
σ=stress profile, also "chaotic" (inherent) stress profile
$\sigma_{perm}$=permissible, desired, defined (inherent) stress profile, also referred to as "σ-specification"
σ+=tensile stress
σ−=compressive stress
$\sigma-_E$=compressive inherent stress
$\sigma+_{peak}$=Stress peak or amplitude of tensile stresses
$\sigma+_x$=axial stress
σ+y=transverse stress
$i_{var}$=variable gear teeth
$i_{constant}$=constant gear teeth ±p1=variable beam pressure
a1=axial stress value beginning
a2=transverse stress value beginning
b1=axial stress value middle
b2=transverse stress value center
c1=axial stress value end
c2=transverse stress value end

The invention claimed is:

1. A method for machining a rack made of a metallic material (1), comprising the steps of:

after hardening, or after hardening and straightening, at least in a region of a gear teeth (2) initially a chaotic inherent stress profile (σ) of tensile stresses (σ+) and compressive stresses (σ−) is present, converting the chaotic inherent stress profile (σ) into a more uniform inherent stress profile ($\sigma_{perm}$) without change in microstructure in a functionally combined series of steps of a machining operation, and at least in the region of the gear teeth (2) receiving a pre-stress with defined introduced compressive inherent stresses ($\sigma-_E$) without the tensile stresses (σ+), so that a physical system with stress values of the defined introduced compressive inherent stresses ($\sigma-_E$) and the more uniform inherent stress profile ($\sigma_{perm}$) of a substantially uniform stress distribution or stress plane is present in at least the region of the gear teeth (2), stress peaks ($\sigma+_{peak}$) or amplitudes of the present tensile stresses (σ+) are intentionally eliminated, smoothed or reduced by introducing near-surface inherent compressive stresses ($\sigma-_E$) by shot peening or by inductive heating, after the shot peening or the inductive heating and elimination, smoothing or reduction of the stress peaks ($\sigma+_{peak}$) or amplitudes, the region of the gear teeth (2) attains the pre-stress with the defined introduced compressive inherent stresses ($\sigma-_E$) without the tensile stresses (σ+) by way of subsequent steel wire shot blasting or steel shot blasting as well as steel shot peening, to attain the more uniform inherent stress profile ($\sigma_{perm}$); and wherein after hardening, or after hardening and straightening, the tensile stresses (σ+) and the compressive stresses (σ−) in the range of ±<2.0 MPa×10³ are measured in selectable sections (2.2, 2.3, 2.4), of which at least ±0.5 MPa×10³ are defined as the stress peaks ($\sigma+_{peak}$) or amplitudes.

2. The method of claim 1, wherein after hardening, or after hardening and straightening, in selectable sections (2.2, 2.3, 2.4) in at least one rack (1) of the gear teeth (2), the tensile stresses (σ+) in an axial direction (x) and the compressive stresses (σ−) in a transverse direction (y) in form of measured values of axial stresses (σ+x) and transverse stresses ($\sigma-_y$) are used to define the chaotic inherent stress profile (σ) as a reference stress profile or a theoretically assumed stress profile (σ) for lots, series or sets of the racks (1) to be machined with identical parameters.

3. The method of claim 2, wherein the chaotic inherent stress profile (σ) is measured by X-ray diffraction measurements in at least one near-surface layer of the sections (2.2, 2.3, 2.4) of the gear teeth (2) in the axial direction (x) and the transverse direction (y).

4. The method of claim 2, wherein the axial stresses ($\sigma+_x$) and the transverse stresses ($\sigma-_y$) are measured up to a defined depth of <100 μm.

5. The method of claim 2, wherein the measured values of the axial stresses ($\sigma+_x$) and the transverse stresses ($\sigma-_y$) for the defined chaotic inherent stress profile (σ) as a sample with the reference stress profile or the theoretically assumed stress profile (σ) for the lots or the series of the racks (1) to be machined with the identical parameters.

6. The method of claim 1, wherein the shot peening is performed briefly for <10 s.

7. The method of claim 1, wherein the inductive heating takes place in a range of 120° C.-160° C., and wherein, before the inductive heating and after the inductive heating, values according to respective stress states are measured.

8. The method of claim 1, wherein the values of the defined introduced compressive inherent stresses ($\sigma$-$_E$) are introduced by a beam pressure p1 in a range of ±p1.

9. The method of claim 1, wherein the values of the defined introduced compressive inherent stresses ($\sigma$-$_E$) are in a range of >−0.6 MPa×10$^3$ to <2.0 MPa×10$^3$ present in selectable sections (2.2, 2.3, 2.4).

10. The method of claim 1, wherein the defined introduced compressive inherent stresses ($\sigma$-$_E$) are controlled and detected as a measured intensity by way of an Almen intensity measurement.

11. The method of claim 10, wherein the chaotic inherent stress profile (σ) according to the Almen intensity measurement is used as a reference stress profile or a theoretically assumed stress profile (σ) for lots or series of racks (1) to be machined with identical parameters.

12. The method of claim 1, wherein the chaotic inherent stress profile (σ) of the tensile stresses (σ+) and the compressive stresses (σ−) is converted into the more uniform inherent stress profile ($\sigma_{perm}$) depending on a type of gear teeth (2) or a characteristic of the metallic material of the rack (1).

13. The method according to claim 12, wherein the type of the gear teeth (2) is a uniform or variable gear teeth.

14. The method of claim 1, wherein dimensioning of a diameter (D) of the rack (1) is optimized.

15. The method of claim 14, wherein the rack (1) is a steering rack of a vehicle.

16. The method of claim 1, wherein values of the defined introduced compressive inherent stresses ($\sigma$-$_E$) are in the range of >−0.6 MPa×10$^3$ to <2.0 MPa×10$^3$ present in the gear teeth (2).

17. The method of claim 1, wherein use of the rack (1) with the measured values of the defined introduced compressive inherent stresses ($\sigma$-$_E$) in a range of >−0.6 MPa× 10$^3$ to <2.0 MPa×10$^3$ as a sample for lots or series of the racks (1) to be machined with identical parameters.

18. The method according to claim 1, wherein the shot peening is glass bead blasting.

19. The method according to claim 1, wherein the inductive heating is stress relieving.

* * * * *